(12) United States Patent
Canioni et al.

(10) Patent No.: US 8,599,658 B2
(45) Date of Patent: Dec. 3, 2013

(54) METHOD FOR WRITING AND READING DATA BY FLUORESCENCE ON A LIGHT-SENSITIVE SUBSTRATE, AND RELATED SUBSTRATE AND DEVICES

(75) Inventors: Lionel Stéphane Canioni, Gradignan (FR); Thierry Cardinal, Salles (FR); Bruno Bousquet, Gradignan (FR); Arnaud Royon, Saint-Ciers sur Gironde (FR); Matthieu Bellec, Bordeaux (FR); Kevin Bourhis, Gradignan (FR); Gautier Papon, Aire-sur-Adour (FR); Philippe Legros, Bordeaux (FR)

(73) Assignee: Universite Bordeaux 1, Talence (FR)

( * ) Notice: Subject to any disclaimer, the term of this patent is extended or adjusted under 35 U.S.C. 154(b) by 0 days.

(21) Appl. No.: 13/700,640

(22) PCT Filed: May 27, 2011

(86) PCT No.: PCT/FR2011/051219
§ 371 (c)(1),
(2), (4) Date: Feb. 15, 2013

(87) PCT Pub. No.: WO2011/148113
PCT Pub. Date: Dec. 1, 2011

(65) Prior Publication Data
US 2013/0142021 A1  Jun. 6, 2013

(30) Foreign Application Priority Data
May 28, 2010  (FR) .................................. 10 54177

(51) Int. Cl.
G11B 7/085 (2006.01)
(52) U.S. Cl.
USPC ...................... 369/30.03; 369/272.1; 436/172

(58) Field of Classification Search
USPC .............. 369/108, 95, 53.1, 275.1, 47.1, 100, 369/103, 112.01, 275.4, 283, 112.23, 120; 430/270.1, 280.1; 436/172, 82
See application file for complete search history.

(56) References Cited

U.S. PATENT DOCUMENTS

| | | | |
|---|---|---|---|
| 6,590,852 B1 * | 7/2003 | McCormick, Jr. | 369/112.23 |
| 6,807,138 B1 | 10/2004 | Jamail et al. | |
| 6,950,382 B2 * | 9/2005 | Akselrod et al. | 369/103 |
| 7,072,275 B2 * | 7/2006 | Akselrod et al. | 369/275.1 |
| 7,190,649 B2 * | 3/2007 | Akselrod et al. | 369/53.1 |

(Continued)

FOREIGN PATENT DOCUMENTS

| | | |
|---|---|---|
| EP | 2025406 A1 | 2/2009 |
| WO | WO 00/31733 | 6/2000 |

(Continued)

OTHER PUBLICATIONS

PCT Search Report dated Jul. 11, 2012 for PCT Application No. PCT/FR2011/051219 filed May 27, 2011, 21 pages.

(Continued)

*Primary Examiner* — Ali Neyzari
(74) *Attorney, Agent, or Firm* — Patterson Thuente Pedersen, P.A.

(57) ABSTRACT

A method for 3D recording of data on a medium formed from a transparent photosensitive material including at least one dopant. The method includes a first step of calibrating and checking a pulsed light source including calibrating the number of pulses, the level of fluence of each pulse emitted and the rate of the pulses and a step of inscribing an area of the material. The fluence of each pulse emitted, the number of pulses and the rate of the pulses are suitable for irradiating the material in the area so as to form fluorescent clusters stabilized from the dopant while minimizing the modification of the refractive index and the absorption coefficient of the medium in a wavelength range from visible to near infrared.

8 Claims, 6 Drawing Sheets

(56) References Cited

U.S. PATENT DOCUMENTS

| | | |
|---|---|---|
| 7,919,328 B2 * | 4/2011 | Dejneka et al. ............... 436/172 |
| 2004/0250749 A1 | 12/2004 | Akselrod et al. |
| 2007/0212793 A1 | 9/2007 | Dejneka et al. |

FOREIGN PATENT DOCUMENTS

| | | |
|---|---|---|
| WO | WO 03/048431 A1 | 6/2003 |
| WO | WO 03/077240 A2 | 9/2003 |
| WO | WO 2004/034380 A2 | 4/2004 |
| WO | WO 2004/034380 A3 | 4/2004 |
| WO | WO 2006/007766 A1 | 1/2006 |

OTHER PUBLICATIONS

French Search Report dated Feb. 8, 2011 for French Application No. 1054177 filed May 28, 2010, 5 pages.

Bellec et al., Beat the diffraction limit in 3D direct laser writing in photosensitive glass, Optics Express, vol. 17, No. 12, Jun. 4, 2009, 15 pages.

Canioni et al., Three-dimensional optical data storage using third-harmonic generation in silver zinc phosphate glass, Optics Letters, vol. 33, No. 4, Feb. 15, 2008, pp. 360-362.

Shin et al., Formation and removal of multi-layered fluorescence patterns in gold-ion doped glass, Applied Surface Science 155, 2009, pp. 9754-9757.

Huang et al., Three dimensional optical storage by use of ultrafast laser, Optical Data Storage, 2003, pp. 264-268.

Bellec et al., Silver Clusters as Probes for Femtosecond Laser—Glass Interaction, OSA/CLEO/QELS, 2008, 2 pages.

Maurel et al., Luminescence properties of silver zinc phosphate glasses following different irradiations, Journal of Luminescence 129, 2009, pp. 1514-1518.

* cited by examiner

METHOD FOR WRITING AND READING DATA BY FLUORESCENCE ON A LIGHT-SENSITIVE SUBSTRATE, AND RELATED SUBSTRATE AND DEVICES

PRIORITY CLAIM

The present application is a National Phase entry of PCT Application No. PCT/FR2011/051219, filed May 27, 2011, which claims priority from French Application No. 1054177, filed May 28, 2010, the disclosures of which are hereby incorporated by reference herein in their entirety.

FIELD OF THE INVENTION

The present invention relates to methods of recording and reading data on photosensitive media for high-capacity data storage.

Furthermore, the invention also relates to devices for recording and reading data on such media. Finally, the invention also relates to such media.

More particularly, the field of the invention relates to methods of writing using high-rate pulsed, laser emission for sufficiently irradiating a dopant of a glass medium.

The field of the invention also relates to methods for forming metal clusters in such media and the writing methods implemented by means of suitable lighting of said clusters. The clusters include a signature specific to the radiation thereof.

BACKGROUND

Currently, the data storage methods that are mainly distributed are specially suited to media such as CDs, DVDs or Blu-ray® disks. The method of writing data on such media can be carried out on a few superposed layers of the disk in 2D.

The Blu-ray medium enables the largest 2D data-storage volume, and it is generally close to or slightly greater than 50 Gbits. This capacity is in any case theoretically limited to 100 Gbits.

The generally accepted lifetime of such a medium is 10 years. This limitation is particularly due to the short lifetime of the polymer layer.

Today, for some requirements for storage, particularly for permanent archiving of data, the lifetime and the capacity of the media are too small. This limitation results in an increase in the number of media to meet the archiving and storage requirements.

New 3D data recording techniques have been developed, particularly using multiphoton absorption of a material subjected to the high intensity of a laser beam.

Two 3D recording writing methods are known—a first method of recording by so-called "photochromism" and a second method of recording by so-called "fluorescence" on glass media.

Photochromism recording particularly causes a reversible transformation of the dopant incorporated in a transparent medium. The dopant includes two states depending on the irradiation to which it is subjected, each of the states corresponding to a modification of the absorption coefficient and of the refractive index of the medium. These two states enable the light to be multiplexed differently according to the polarization, wavelength and phase features. These features can be selected such as to use the absorption and refraction properties modifying the waves reflected during lighting for the reading of data and can therefore be used to decode the information read.

A problem of photochromism recording is that reading the information, for example, by using polarization is extremely difficult to control. Indeed, the light for lighting the medium is optionally modified according to the refractive index of the lit area of the medium, but it is extremely difficult to control the polarization of the light on consumer optical components, which results in using error correctors. Furthermore, this technique requires the use of a writing-tuneable laser. Consequently, it is difficult to implement and it is expensive. Finally, the gain in the storage of data is not large enough in view of the implementation of such a solution.

Fluorescence recording has never been implemented since it has never been possible to stabilize the fluorescent species in a transparent medium. This limitation is due to the modification of the intensity of fluorescence over time particularly resulting from processes of reading the medium which consist of successive lighting. Fluorescence recording could not then allow stability and permanence of the encoded information.

Consequently, this type of technology did not enable until now an area of a transparent medium to be irradiated with a view to encoding information at the level of the fluorescence of the photo-induced species.

Furthermore, irradiation generally brings about a modification of the refractive index which does not enable reading of the data in 3D due to the diffusion of the light of the irradiated areas.

SUMMARY

The invention enables the aforementioned disadvantages to be overcome. Particularly, the data 3D recording method of the invention enables information to be recorded on a medium formed from a transparent photosensitive material including at least one photosensitive dopant. The recording method of the invention particularly includes:
- a first step of calibrating and checking a pulsed light source including calibrating the number of pulses, the level of fluence of each pulse emitted and the rate of the pulses;
- a step of inscribing an area of the material.

The method of the invention enables definition of the fluence of each pulse emitted, the number of pulses and the rate of the pulses such that the irradiation enables formation of the fluorescent clusters stabilized from the dopant while minimizing the modification of the refractive index and the absorption coefficient of the medium in a wavelength range from visible to near infrared.

Furthermore, the invention includes a method of reading on a medium information recorded with the recording method of the invention.

The reading method of the invention enables reading of a modified transparent medium locally comprising a set of 3D-arranged stabilized metal ion clusters, each of the clusters emitting fluorescence during luminous excitation.

The reading method includes:
- a step of lighting by a second source of light focused in an area of the medium for a first duration $t_1$, the set of the clusters of a same area being called an "emitter" and;
- a second step of capturing the luminous intensity re-emitted by the emitter for a second duration $t_2$.

Advantageously, the method for 3D recording of data on a medium formed from a transparent photosensitive material including at least one dopant, includes:

a first step of calibrating and checking a first pulsed light source including calibrating the number of pulses, the level of fluence of each pulse emitted and the rate of the pulses;

a step of inscribing an area of the material.

Advantageously, the fluence of each pulse emitted, the number of pulses and the rate of the pulses are suitable for irradiating the material in said area so as to form fluorescent clusters stabilized from the dopant while minimizing the modification of the refractive index and the absorption coefficient of the medium in a wavelength range from visible to near infrared.

Advantageously, the first source of light is calibrated such that:

the rate of the pulses is greater than a second predetermined threshold for creating a temperature that is greater than a third temperature predetermined threshold in the irradiated area;

the duration of each emitted light pulse is shorter than the characteristic time of thermalization of the material such as to excite the area of the medium by multiphoton ionization.

Advantageously, each cluster forms a fluorescent emitter, the spectrum and the intensity of fluorescence of which correspond to a signature for encoding a data word, said stabilized clusters.

Advantageously:

the rate of each pulse of the first light source is greater than 1 kHz; and more particularly greater than 10 kHz where the thermal effects in the material are better particularly since the material no longer has the time to cool;

the fluence of each pulse transmitted is substantially close to $1 \ \text{J} \cdot \text{cm}^{-2}$;

the wavelength of the laser is at least two times greater than the cut-off wavelength of the transparent medium.

Advantageously, the first light source includes at least one of the two following light sources: an infrared femtosecond laser, an infrared picosecond laser.

Advantageously, the medium is formed from a glassy material and the dopant includes at least one type of metal ion of the set of following ions: silver ion, noted Ag, gold ion, noted Au, copper ion, noted Cu.

Advantageously, the irradiation step comprises a set of pulses on a same area of the medium so as to form stable irradiated clusters, the formed clusters defining a fluorescent emitter, the spectrum and the intensity of fluorescence of which, corresponding to a given calibration of the first light source, defines a signature.

Advantageously, the rate of the pulses of the first light source is substantially equal to 10 MHz.

Advantageously, the steps of the recording method are repeated on a set of areas located at a same depth of the medium, the set of the areas located at a same depth being called a layer, each calibration of the first source being suitable for an inscription given on each of the areas, wherein the method can be repeated on superposed layers of the medium.

Advantageously, the invention relates to a device for recording data of a data storage transparent medium formed from a material comprising a dopant.

Advantageously, the recording device includes a femtosecond laser emitting a pulsed beam for irradiating an area of the medium, the rate and the number of the pulses being controlled by means of a light modulation device, the irradiation being carried out by means of an objective for focusing the laser light locally in an area of the medium, the pulse transmitting an energy to the medium ionizing the material at the focal point of the microscope, the recording device comprising motive means for moving the medium in relation to the light source such as to successively repeat the steps of the method of the invention on a set of areas in 3D.

Advantageously, the invention relates to a data storage transparent medium formed from a material comprising at least one dopant. Advantageously, the material comprises stable irradiated clusters, said clusters forming a fluorescent emitter, the spectrum and the intensity of fluorescence of which correspond to a signature for encoding a data word.

Advantageously, the transparent medium can be:

an analogue optical disk;

an electrode;

a calibration plate for a fluorescence microscope;

a fluorescent lamp;

a watch glass.

Advantageously, the invention relates to a method of reading a transparent medium formed from a modified material comprising locally a set of stabilized clusters inscribed in 3D in the material, each of the clusters emitting fluorescence during luminous excitation.

Advantageously, the reading method includes:

a step of lighting by a second source of light focused in an area of the medium, the set of the clusters of a same area being called an "emitter";

a second step of capturing the luminous intensity re-emitted by the emitter and;

a decoding step for associating a fluorescence intensity with a data word.

Advantageously, the method of reading a modified transparent medium includes a third step of filtering the excitation light of the re-emitted light for capturing solely the visible fluorescent light.

Advantageously, the medium includes a plurality of superposed layers formed in the material, one layer including a set of areas of a same depth in the material, the first step being carried out by means of confocal filtering for distinguishing the fluorescent light emitted by an emitter of an area of a given layer from that emitted by an area of another layer.

Advantageously, the invention further relates to a device for reading data of a data storage transparent medium comprising at least one dopant. Advantageously, the reading device includes a laser diode lighting, in the range 330 nm-450 nm, an area of the medium comprising a set of fluorescent clusters, the set of the clusters of one area being called an emitter, the reading device comprising means for collecting various levels of luminous intensity emitted by fluorescence of the lit emitters and means for converting the luminescence into a digital signal such as to form a data word corresponding to the spectrum and to the intensity of fluorescence, the reading device including, furthermore, motive means for moving the medium in relation to the light source such as to successively repeat the steps of the reading method of the invention on a set of areas of at least one layer of the medium.

Advantageously, the 3D calibration plate for an optical system includes at least one stable fluorescent cluster, the intensity and the spectrum of which enables definition of the features of a calibration test chart for checking at least one of the following features of a measurement optical system corresponding to response functions of an optical system:

the levels of fluorescence intensity;

the uniformity of the field of view;

the colour response;

the time response function through the calibration of the dynamics of the sensors.

Advantageously, the optical system is a system from the following list: microscope, detectors, light sources.

Advantageously, the test chart enables calibration of the system for positioning the optical components of the optical system.

Advantageously, the test chart enables calibration of the optical resolution of the optical system.

Furthermore, the invention includes a recording device, a reading device and a medium for implementing the recording and reading methods of the invention.

BRIEF DESCRIPTION OF THE DRAWINGS

Other features and advantages of the invention will be presented in a detailed description illustrated by the following figures: the following description is given with reference to the appended drawings wherein.

DETAILED DESCRIPTION

The methods of the invention which are successively described, include:
- a method of recording data on a transparent medium doped with a view to meeting storage high-capacity requirements and;
- a method of reading data on such a medium.

The devices of the invention which are described successively relate to:
- a device for recording data on a transparent medium doped with a view to meeting storage high-capacity requirements and;
- a device for reading data on such a medium.

A data storage transparent medium comprising stable photo-induced clusters, said clusters of a predetermined area forming a fluorescent emitter, the spectrum and the intensity of which correspond to a signature.

The data recording method of the invention enables data to be recorded on a medium formed from a transparent photosensitive material comprising at least one dopant.

The recording method comprises a first step of calibrating:
- the fluence of a pulsed light source, the fluence being the emitted energy area density;
- the rate of the pulses and;
- the number of pulses emitted in the irradiated area.

Furthermore, the recording method of the invention comprises a step of irradiating an area of the medium. In this step, the fluence of each pulse, the number of pulses and the rate of the pulses are suitable for irradiating, in said area, part of the material such as to form clusters stabilized from the dopant while minimizing the modification of the refractive index of the medium.

The rate of the pulses emitted is a laser configuration datum which is also called the laser repetition rate.

The recording method of the invention can further comprise a step of repeating the two first steps on a set of areas of the medium. One advantage of the invention is that the areas can be located at various depths and consequently the data recording method is a 3D method which enables the storage capacity of the medium to be significantly increased.

Figure 1:
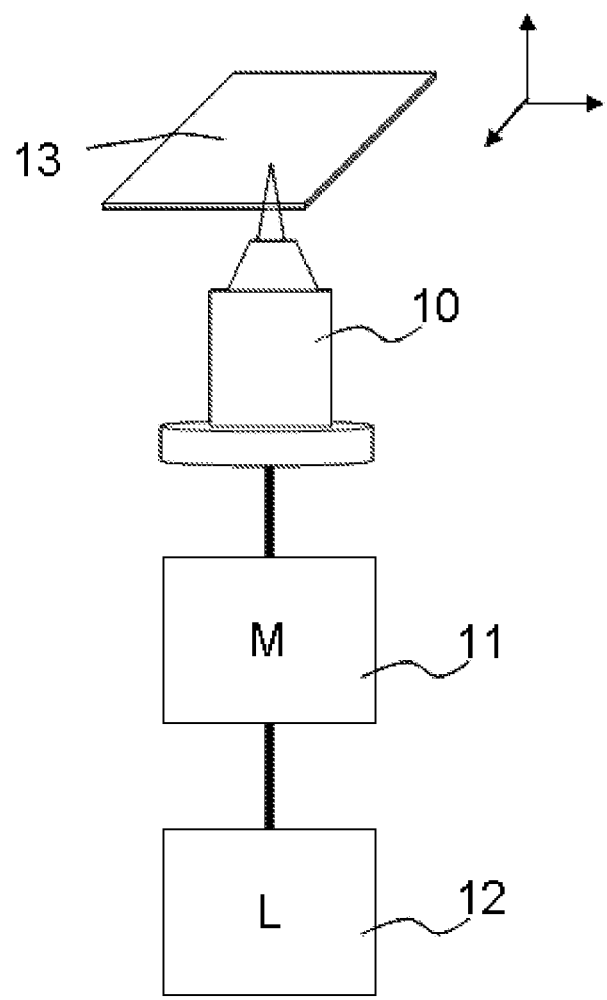
FIG. 1 shows a data recording device of the invention.

FIG. 1 shows means for implementing the data recording method of the invention, particularly:
- a laser 12, noted L, for generating a laser beam on an interaction area of a transparent medium 13, which area is doped with metal ions;
- an acousto-optic modulator 11, noted M, for varying the repetition rate of the laser or the number of pulses per interaction area of the medium 13;
- a microscope objective 10 for focusing the laser beam in the desired interaction area of the medium 13.

The function of the microscope objective can be carried out by any means of a focusing element like a microscope objective or a lens.

In a particular and preferred embodiment of the invention,
- the transparent medium is a photosensitive glass doped with silver ions;
- the laser is a femtosecond laser emitting in the infrared range at an energy such that, at the focal point, a fluence close to 1 $J \cdot cm^{-2}$ per pulse is generated.

In another embodiment, the laser is a picosecond laser. The invention can be implemented once the duration of the pulse is less than or equal to a picosecond.

The wavelength of the laser and the cut-off wavelength of the glass, the wavelength from which the glass absorbs light, are selected such that the wavelength of the laser is much greater than the cut-off wavelength of the glass, i.e., at least twice as great.

For example, the wavelength of the laser can be selected close to 1030 nm for a cut-off wavelength of the glass which is substantially close to 270 nm.

The data recording method includes a configuration such that the repetition rate of the laser is a value greater than 1 kHz and more advantageously greater than 10 kHz. Indeed, beyond this frequency, the material no longer has the time to cool between two pulses and the thermal effects are more favourable to the formation of clusters. This configuration can be obtained from a light modulation device such as an acousto-optic modulator 11.

A preferential embodiment enables the value of the repetition rate to be set to a value substantially close to 10 MHz. This configuration enables, when the data recording method of the invention is executed, the irradiated particles of the material of the medium to be stabilized.

The photosensitization of the glass is a non-linear phenomenon caused by the multiphoton absorption of the material which enables formation of the clusters of irradiated particles, called species.

Proximate to the waist of the beam focused by the microscope objective 10, the fluence is sufficient to create an image, called a "latent image". Unlike other irradiation techniques such as those obtained from UV emissions, from X-rays, gamma rays, or by emission of electron beams, the energy of the laser is deposited in the material more quickly than the characteristic time of thermalization for the irradiated particles.

This feature specific to the configuration of the recording method of the invention enables the species to be stabilized.

Figure 2:
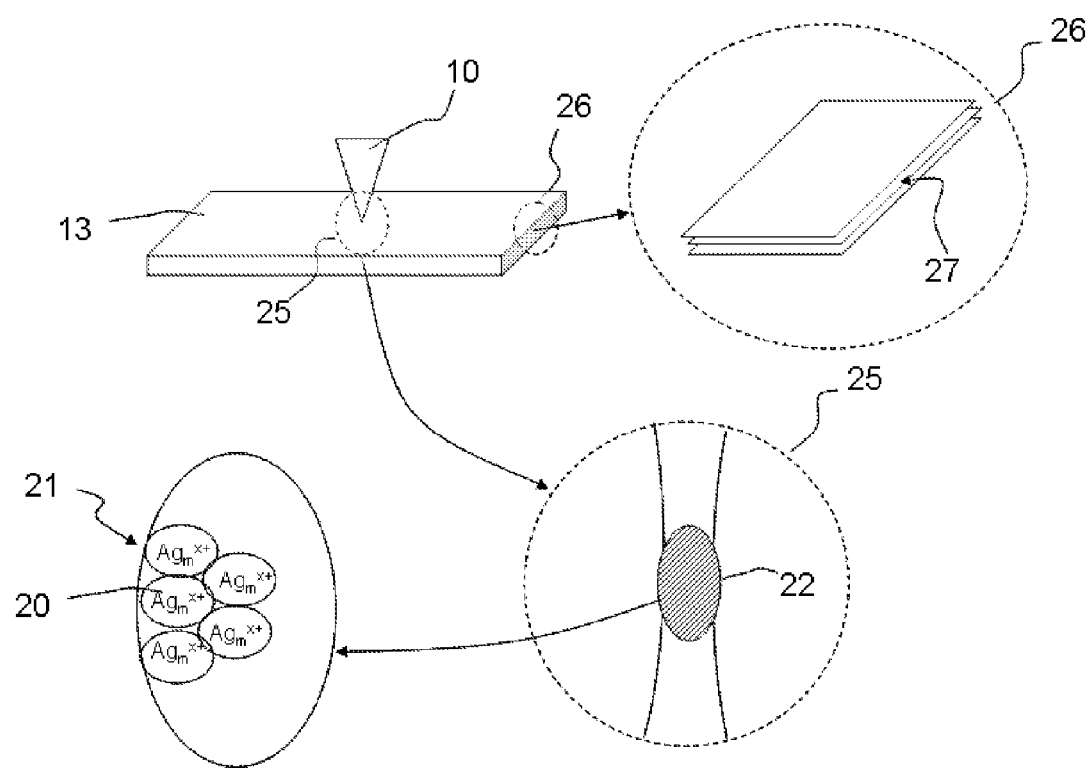
FIG. 2 shows the formation of irradiated clusters according to the recording method of the invention.
Figure 3:
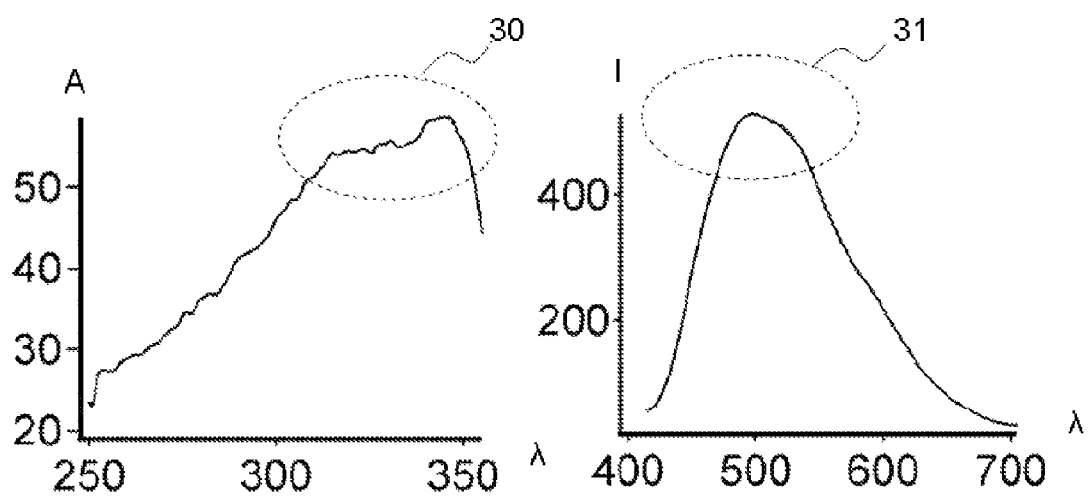
FIG. 3 shows the absorption and emission spectra of an irradiated area of a medium of the invention.

FIG. 2 shows microscope optical components 10 for focusing the laser in an interaction area 25 of the medium 13. In the example of FIG. 3, the clusters 21 which are formed in the waist 22 of the beam at a given depth of the material of the medium are silver $Ag_m^{x+}$ irradiated particles 20. The irradiated particles which are formed are stabilized in the material.

The clusters formed in an irradiated area define a fluorescent emitter, the spectrum and the intensity of fluorescence of which enable a signature to be defined.

The recording method of the invention enables, from the calibration step, the irradiation parameters to be defined, such as particularly the fluence, the number of pulses and the laser repetition rate. From the irradiation parameters, the recording method of the invention enables, from a certain number of laser pulses, a fluorescent emitter to be created in an interaction area. The emitter is defined by a spectrum and an intensity of fluorescence specific to the irradiated area defining therefore a signature of the irradiated area.

Particularly, the irradiation step comprises a set of pulses on a same area of the medium so as to form stable irradiated clusters in said area.

When the clusters are lit, they emit in turn a fluorescent light. The fluorescent luminous intensity emitted by the clusters corresponds to a signature which can particularly be read by interpretation of the re-emitted spectrum using a data reading method of the invention described hereafter.

Consequently, the configuration of the irradiation, including the fluence, the number of pulses and the rate of the pulses, of a given area of the medium defines a grey level corresponding to a fluorescence level of the clusters formed in said area when they emit in turn a luminescence.

An embodiment of the data recording device of the invention includes a femtosecond laser emitting a pulsed beam for irradiating an area of the medium, the rate of the pulses, also called the repetition rate, being produced by means of an acousto-optic modulator.

The irradiation is preferably produced by means of a microscope objective for focusing the laser light locally on an area of the medium. The laser pulse transmits an energy to the medium ionizing the dopant in an area close to the focal point of the microscope.

The recording device further comprises motive means for moving the medium in relation to the light source such as to repeat successively the irradiation step of the recording method of the invention on a set of areas of the medium while adjusting the fluence, the number of pulses and the rate of the pulses at each irradiated area.

The areas can, for example, be organized by layer in the material when they are located at a same depth. Advantageously, the medium can include a plurality of superposed layers.

FIG. 2 shows a sample 26 of the medium wherein several layers 27 can be superposed such as to organize the recording of the data per stratum in the medium. The information reading method of the invention is then implemented by a series of operations for reading an area in a same layer and from one layer to another layer.

The acousto-optic modulator also enables variation of the laser repetition rate or the number of pulses per interaction area.

In an embodiment of the device, the microscope objective focuses the laser beam with a numerical aperture of 0.52, which corresponds to a focal spot with a 2 μm diameter. The stage motorized on 3 axes enables the waist of the beam to be positioned in an irradiation area, forming a volume-defined material sample, the irradiation taking place with a precision of 50 nm on the irradiated volume.

After irradiation according to the recording method, the glass is modified and comprises a so-called latent image since it is only visible by fluorescence microscopy, without apparent modification of index.

The intensity of fluorescence of the clusters particularly depends on the intensity of the incident laser beam and on the number of pulses.

FIG. 3 shows a first graph showing the absorption spectrum $A(\lambda)$ of the irradiated area, where A is the absorption and $\lambda$ the wavelength.

FIG. 3 shows a second graph showing the emission spectrum $I(\lambda)$ of an irradiated area of the glass, where I is the intensity emitted by the lit clusters.

The method of the invention enables a medium to be formed wherein the material is modified, the pulse laser irradiation having created small stabilized clusters forming a latent image.

In a preferred embodiment, the clusters are clusters of $Ag_m^{x+}$ silver where m<8 and x<2.

In other embodiments, the metal clusters are gold or copper clusters. In one particular embodiment, the material includes ions of various kinds such as gold, copper or silver in different or equal amounts.

The absorption spectrum of the first graph particularly has a first area 30 of absorption centered between 320 nm and 400 nm.

The emission spectrum of the second graph has a band centered at 500 nm. The fluorescence of the irradiated species enables a signature to be defined. These species have absorptions between 300 and 400 nm and a white emission visible broadband emission.

The lifetime of the fluorescence is approximately three nanoseconds. The white fluorescence is intense and can in some cases be observed with the naked eye.

The pulse laser irradiation like the other types of irradiation enables small metal clusters to be created in the photosensitive glass. In the case of the femtosecond laser, for large repetition, for example above 10 kHz, the increase in temperature in the glass is greater than 300° C. This temperature is sufficient for the process of diffusion of the silver to start. An increased temperature close to 350° C. in the irradiation area contributes to obtaining good conditions for stabilization of the species.

The clusters that are formed as a result of the irradiation enable the neutral atoms of silver $Ag^0$ to be stabilized outside of the thermodynamic equilibrium thereof.

The method of the invention enables an intensity of the femtosecond laser to be generated such that at the center of the waist of the beam, the clusters cannot last since they are photodissociated by multiphoton effect.

The method of the invention therefore enables the diffusion of the photosensitive agent to be forced from the center of the laser beam to the periphery where the intensity is not sufficient to separate the clusters.

The recording method of the invention enables the diffusion at the periphery of the irradiated area to be stopped since the created chemical species of silver $Ag_m^{x+}$ stabilize said area.

These clusters practically do not diffuse as a result of the size thereof. Finally, with the recording method of the invention, an image that is latent at the focus of the beam is created. This image is erased at the center at the same time that it is created. Only an image at the periphery of the area lasts and intensifies with the exposure time by diffusion.

An embodiment of the invention enables information to be recorded on the medium by irradiation of areas located at a same depth of the material. The latter then form a layer in the material.

The method of the invention then enables the information to be recorded in the material at various depths such that various layers including data can be superposed, the irradiation of an area of a layer having no effect on the areas of superposed layers when they are separated by a few micrometers.

One embodiment is obtained by repeating the method in various areas, for example which are selected adjacent and one after another in the material at a same depth. The intensity of the laser beam emitted is set constant at $20 \times 10^{12}$ W·cm$^{-2}$ and a number of pulses is emitted in an increasing manner from a first area up to a last area from $10^2$ to $10^7$ pulses per irradiated area.

In this embodiment, the method of the invention enables areas to be created which each comprise one grey level from 256 grey levels, the grey level being measured after lighting the areas, during re-emission of a fluorescent intensity of the clusters contained in each area.

An advantage of the recording method of the invention is that the emission spectra and the intensity of fluorescence of the clusters do not vary after exposure under a violet laser beam with a light power of 150 mW and a wavelength of 405 nm for millions of reading cycles.

Furthermore, there is no notable deterioration of the fluorescence properties even up to a temperature of 350° C. Finally, the glassy medium is time-resistant, to approximately several thousand years, which is much greater than the other media that are currently available which are time-resistant to approximately a few dozen years.

The invention also relates to a transparent medium for storing data and a method of reading data of said medium.

The transparent medium of the invention is formed from a modified material. The medium comprises at least one latent image formed by a set of metal ion clusters that are distributed locally in the volume of the medium and are stabilized. Each of the clusters behaves like a fluorescent emitting source, the set of the clusters of a same area being called an emitter, when the area is excited by a suitable light source.

The data reading method of the invention includes:
a step of lighting by a second source of light focused in an area of the medium for a first duration ($t_1$) and;
a second step of capturing the luminous intensity re-emitted by the emitter for a second duration ($t_2$).

The second duration $t_2$ can, in one embodiment, be substantially around the same length as the lifetime of the fluorescence of the emitter.

The method optionally comprises a third step of filtering the violet excitation light of the fluorescent light re-emitted by the emitters. Filtering the violet light enables only the visible fluorescent light to be captured by the reading device according to the invention detailed hereafter.

When the medium comprises several superposed layers, the first step can be carried out by means of confocal filtering for focusing the light emitted by the second source at the depth of one of the layers.

An advantage of the reading method of the invention is that it does not require a radical change in technology compared with the currently used methods. For example, current Blu-ray technology can be adapted particularly with regard to the emission wavelength of the second light source.

An emission wavelength of the second source close to 405 nm is compatible with the band for exciting the photo-induced species in the reading method of the invention.

The numerical aperture of the lens, for example an aperture of 0.85, is sufficient to be able to distinguish layers separated by a few micrometers. The strong intensity of the signal does not require a change of sensor.

The data reading method of the invention advantageously comprises a fourth step of analogue/digital conversion for distinguishing a level of fluorescence luminous intensity such as to form a corresponding data word.

An advantage of distinguishing a digitized grey level is the possibility of encoding the information on several levels therefore increasing the quantity of information contained in the medium.

Finally, in the embodiment of the invention wherein the medium includes a plurality of superposed layers, it is possible, during the data reading method, to use confocal filtering in order to limit the interlayer interactions. This phenomenon is also called "cross-talk".

The invention relates to a data reading device.

Preferentially, the data reading device includes a laser diode lighting, in the range 330 nm-450 nm, an area comprising stabilized fluorescent clusters in a medium. The set of the clusters of a same area defines a fluorescent emitter. Furthermore, the reading device comprises means for capturing the luminous intensity emitted by fluorescence by an emitter and means for converting the luminescence or the fluorescence into a digital signal such as to form a data word corresponding to the spectrum and to the intensity of the emitter.

Finally, the reading device includes motive means for moving the medium in relation to the light source such as to repeat successively the steps of the reading method on a set of areas of at least one layer of the medium and advantageously on various layers of the medium.

In other embodiments, it is also possible to use laser diodes having a wavelength shorter than 405 nm and lenses allowing a large numeric aperture such as to improve the performance of reading data on the medium.

An advantage of the data reading device and method is that the reading speed is limited by the lifetime of the fluorescence, i.e., 500 Mbits·s$^{-1}$.

Finally, the use of a glassy medium enables permanent media to be obtained for durations of several dozen years. Particularly, the use of a glass gives far greater stability performance than a polymer particularly doped with an organic dye which has low stability properties linked to photobleaching. This disadvantage limits proper preservation of the recorded data.

Glass is not suitable to be used with an organic dye, particularly since the latter cannot be used as a dopant with glass.

One alternative of the invention is the use of a polymer medium with silver ions for example.

According to the recording method of the invention, silver clusters are formed, but they will be less stable over time than with the use of a glass medium. The storage of data is less permanent.

The glass medium has real advantages with regard to the gain in stability and permanence of the medium, since the emitters are stabilized by the glassy matrix, which cannot be the case in polymers.

One use of the invention, particularly of a medium of the invention, is to enable a calibration plate for fluorescence microscopy to be manufactured. For example, the various microscopy optical platforms have a need to calibrate and deconvolve the images thereof taken by confocal microscopy with laser scanning of calibration test charts for determining perfectly the response function of the optical system thereof in 3D. The platforms also require fluorescent reference objects which are stable over time. Indeed, the response of the photodetectors, the misalignment of the instruments, and the photobleaching of the fluorescent species bring about difficulties of comparing images taken at separate locations and times.

Furthermore, the invention can be adapted to the measurement of an electric current. Particularly, the stability of the fluorescent centers at high temperature enables uses to be envisaged for patch fluorescent electrodes. For example, in neurobiology, when an electric current flows between two electrodes made up of silver clusters, which electrodes are implanted on a biological system, these clusters emit fluorescent light, the intensity of which depends on the electric current. Therefore, very small electric currents (or differences in potential) can be measured thanks to this type of electrode.

In this last mode of use, advantageously the medium is an electrode, for example.

Another use of the invention enables the recording method of the invention to be used for engraving a signature of a glass medium. Advantageously, the method can be used in the fight against counterfeiting.

The laser inscription in the glass is not visible to the eye, but only when it is excited with a blue laser diode as fluorescence.

The method of the invention enables inscriptions in "data matrix" form to be recorded on a medium. An advantage is that it enables high-density data recording.

The data matrix code is a high-density two-dimensional symbology for showing a large quantity of information on a small surface—up to 2335 alphanumeric characters or 3116 numeric characters, on approximately 1 $cm^2$.

Another advantage of the data matrix code is that it is in the public domain and is free by right. Furthermore, it meets the IEC 16022 standard.

Typically, this signature in glass incorporated into objects enables them to be simply identified while retaining a visible outer appearance with no sign of data inscription.

The method can therefore be used for any type of object including a glass part. Particularly, it is advantageous to produce such engraving on luxury objects such as a watch, a bottle or a pair of glasses.

In this last case, the reader for identifying the data matrix code is a reading device as defined in the invention. It can be an onboard reader and miniaturized such as to be transportable in a simple manner.

The reading method of the invention enables the inscription on the medium of the invention to be decoded.

Another use of the invention is the manufacture of an optical analogue disk medium of the invention. This medium can be advantageously similar to vinyl records.

The reading device of the invention enables the diamond stylus normally used during the reading of a vinyl record to be advantageously replaced with a UV laser, on fluorescent tracks, the intensity of fluorescence of which corresponds to an analogue level.

Finally, a use of the invention enables fluorescent lighting to be manufactured. In this case, the medium is a fluorescent emitter. By exciting the emitters made up of silver clusters with an electric current, the latter emit fluorescence, in the same manner as light-emitting diodes.

According to a particularly advantageous embodiment, a percentage of dopant in the glass is greater than 4%. This proportion enables an optimum configuration, particularly such as to increase the stability of the clusters in the glass.

The stability of the clusters is also improved when the pulses of the laser have a luminous intensity which is configured between 1 and 5 $J/cm^2$. The number of pulses is also advantageously suitable to obtain a local temperature during the writing process, the temperature being close to 300° C., typically greater than 100° C.

During the use of the invention for manufacturing microscope calibration plates as mentioned above, various embodiments can be implemented.

Particularly, according to the embodiments which can be combined, fluorescent clusters can be created and arranged in a calibration plate such as to form test charts having particular properties. Depending on the configurations, the test charts enable the field homogeneity, the lateral resolution, the response of the detectors, the lifetime of the fluorescence, the repositioning of the stages, the depth of field or the longitudinal and axial resolution, and the stability of the laser to be calibrated.

Figure 4:
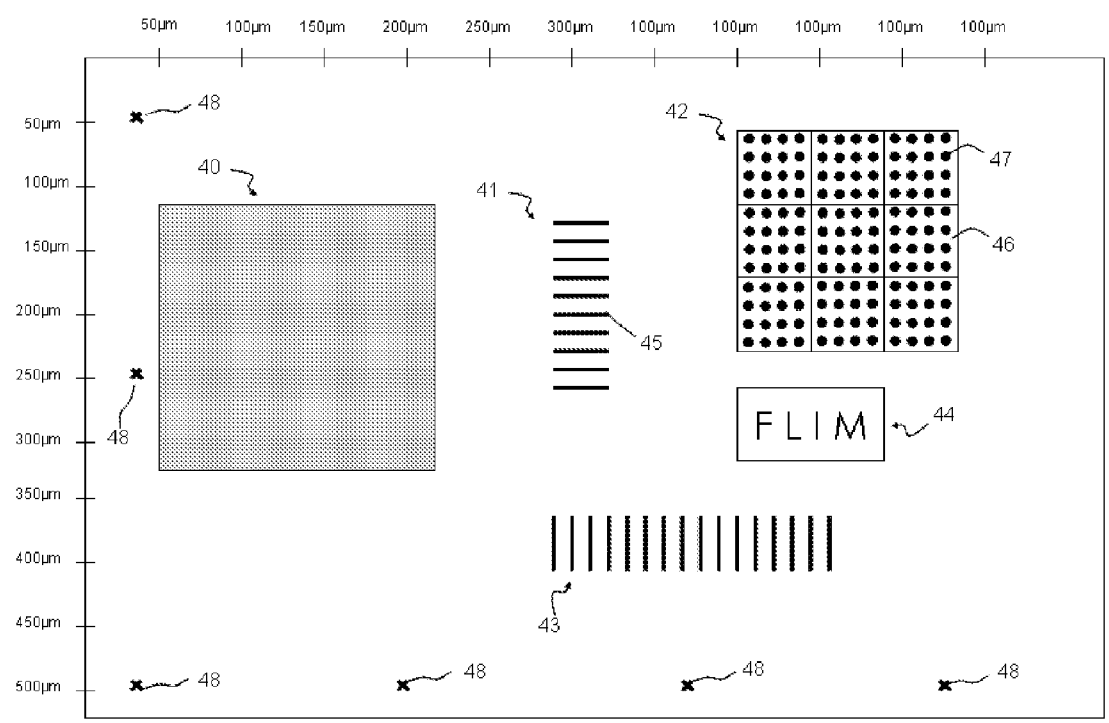
FIG. 4 shows various types of test charts formed by fluorescent clusters of the invention.

FIG. 4 shows a calibration plate including various arrangements of clusters for calibrating the microscope. A given arrangement of clusters is called a "test chart". The latter forms a 2D or 3D pattern engraved at a given depth or at various depths of the plate. The inscription is carried out using the method of the invention such that the clusters form a data word. For use in a calibration plate, a data word can correspond to a given fluorescence intensity. A data word is, for example, encoded as a function of the luminescence level re-emitted after lighting of the cluster.

In a glass medium, the advantage of the formation of the fluorescent clusters is that they remain stable over time. A data word formed by a fluorescent cluster is not modified by photobleaching or any other phenomenon which can alter the properties of a cluster. Particularly, the method of the invention enables the clusters which are directly formed and trapped in the medium to be not altered. The stability of the clusters enables fluorescence microscope calibration plates which are reliable to be produced and a high level of precision of the calibrations to be obtained.

FIG. 4 shows a first uniform test chart 40. To this end, the data recording method of the invention enables engraving, uniformly on the whole field, of clusters which have the same properties and are evenly distributed over a given surface and at a given depth of the plate. This test chart enables the homogenization of a field to be calibrated during the calibration of a microscope.

Figure 5:
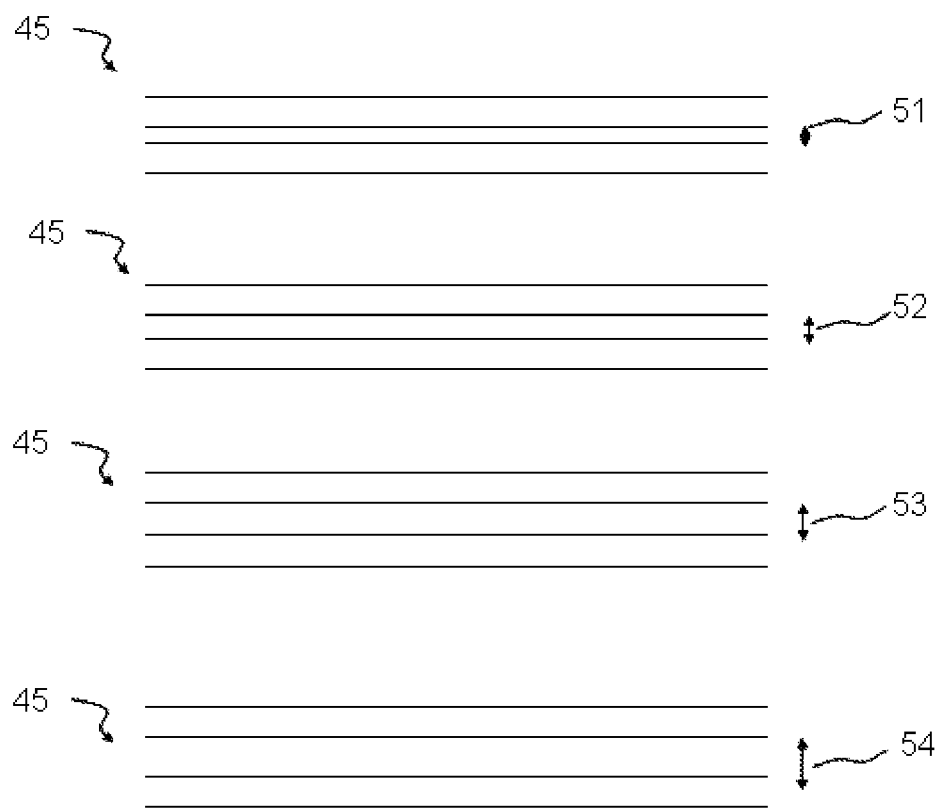
FIG. 5 shows a zoom of a test chart forming linear portions.

A second example of a test chart 41 is shown in FIG. 4. The test charts 41 enable the optical resolution of the objectives of the microscopes to be calibrated. The test chart 41 includes a series of horizontal linear sections 45 engraved in 3D in a glass medium according to the method of the invention. Each visible linear section 45 of the test chart 41 includes four lines, the spacing of which is extremely small and is about the size of the width of the lines. Some of the linear sections of the test chart 41 are shown in FIG. 5. FIG. 5 is a zoom of part of the test chart 41.

Firstly, the shape of a cluster engraved according to the method of the invention is to be considered. A cluster engraved according to the method of the invention forms a kind of ring 62 shown in FIG. 6 having a diameter of approximately 1.6 μm. In 3D, this is a tubular structure. The analysis of the dispersion and of the noise of record reading enables an intensity level curve to be displayed for encoding various values. It is possible, for example, to encode the clusters such as to obtain 16 levels of values corresponding to 16 given fluorescent intensities. These levels can be obtained by increasing the number of pulses of a laser, the intensity of which is approximately 5 $J/cm^2$ during the data recording method according to the invention. Therefore, an image can also be encoded in this manner where each pixel is recorded in the volume in the form of a fluorescent tube.

Figure 6:
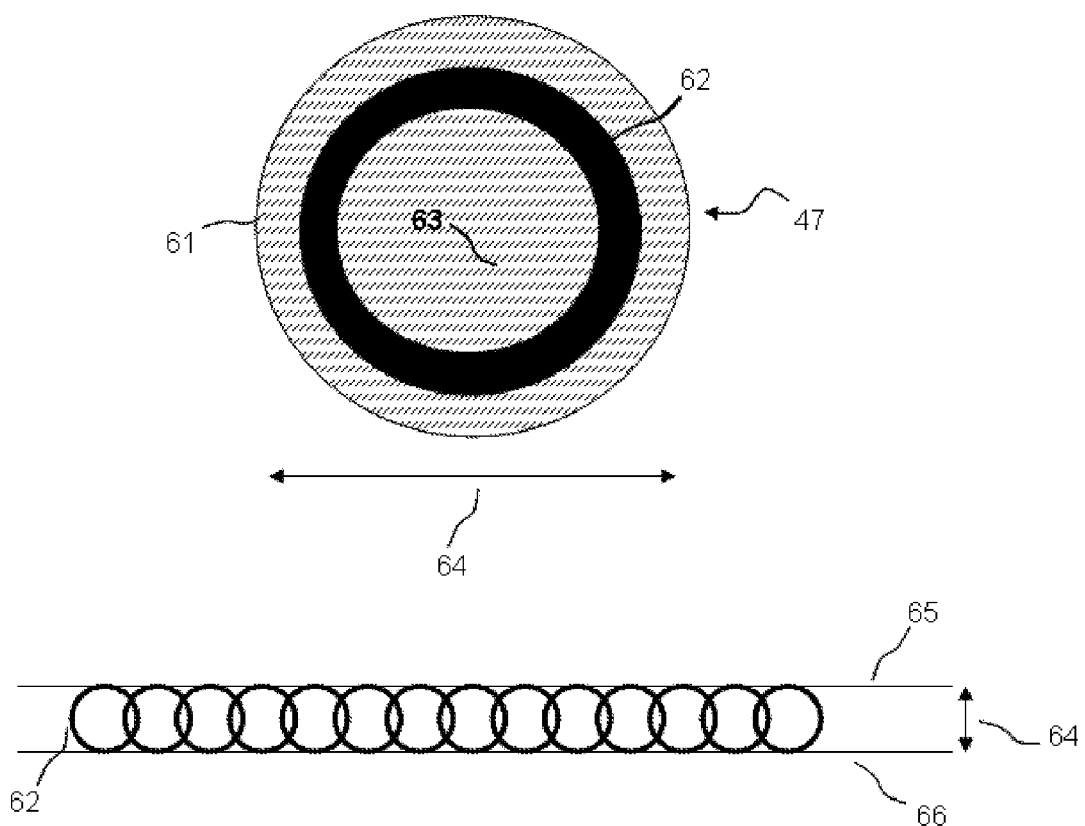
FIG. 6 shows a zoom of a fluorescent cluster formed according to the method of the invention.

The area close to the ring includes a central part 63 and an outer part 61 which are a little less irradiated than the part forming the ring. During the engraving of a test chart 41, i.e., during the implementation of the recording method of the invention to produce linear sections, the clusters are engraved in order to form a horizontal linear track for calibrating the optical resolution of a microscope. In reality, two lines 65, 66 appear in the medium, which are shown in FIG. 6 and correspond to the track of a ring, the recording method of which has been repeated by following a horizontal straight line. The linear track includes two lines spaced by the diameter of the ring of approximately 1.6 µm.

FIG. 5 shows a first linear section 45 including two linear tracks each forming two straight lines. Therefore, there are four straight lines shown. Each of the tracks is spaced by a first spacing 51.

The second linear section, shown below the first section, includes two linear tracks each forming two straight lines, each of the tracks being spaced by a second spacing 52.

The third linear section shown below the second section includes two linear tracks each forming two straight lines, each of the tracks being spaced by a third spacing 53.

The fourth linear section shown below the third section includes two linear tracks each forming two straight lines, each of the tracks being spaced by a fourth spacing 54.

Therefore, it is possible to configure the test chart 41 such that the linear sections positioned under one another include a spacing between the two linear tracks which increases from one section to another.

Typically, a first section includes a spacing substantially close to 100 nm up to a last section, the spacing of which is approximately 2 µm.

A third example allows a test chart 42 to be considered which forms a grid of nine squares or rectangles including a plurality of evenly distributed clusters. The test chart is preferably engraved at a depth of 170 µm. This last depth is optimally suited to fluorescence microscopes and therefore enables focusing that is as close as possible to the normal microscopy observation conditions.

The test chart 42 enables calibration of the photomultipliers and/or of the laser. Indeed, each square of the test chart 42 includes a given fluorescence intensity, i.e., the lighting of a square by an outer light source produces a light emission of the fluorescent clusters which is indeed determined at a certain luminosity. For each of the squares, the clusters of a same square have the same features. Namely, the irradiation of the plate in order to form the clusters has been carried out with the same number of pulses and an intensity selected such as to obtain a given fluorescence intensity per unit area.

Each of the squares in the example of FIG. 4 includes 16 fluorescent clusters, the irradiation of which in a same square enable homogenization of the properties for each of the squares. As a result, each square can emit a given fluorescence intensity after suitable lighting. Various configurations are possible and can be produced as regards the number of squares, the arrangement thereof and the number of clusters per square.

An advantage of this test chart is that it is a fluorescence-invariable reference for calibrating and comparing fluorescence microscopes with one another. This is particularly thanks to the high level of stability of the clusters formed in the calibration plate but also to the invariability of the level of fluorescence emitted by each of the squares which enable various values to be calibrated. Since the fluorescent light source is included in the plate, this test chart enables all of the disadvantages of the methods of calibration by lighting and reflection of a light beam on the plate to be overcome.

In one example, each square has an increasing intensity of fluorescence for creating a scale of reference values.

A fourth example of a test chart 43 is shown in FIG. 4. The test chart 43 shows vertical lines engraved in the plate at various depths depending on the lines. This test chart 43 enables 3D calibration which precisely gives the depth of field of a microscope objective. The precision on the calibration of the measurement of optical components for depth of field is approximately a few hundred nanometers.

Finally, a fifth test chart 44 enables calibration of the time response of the detectors through the measurement of the lifetime of the fluorescence after exciting the clusters and observing the time of arrival on the detector of the photons emitted by these same clusters. This test chart enables the system for measuring the fluorescence lifetime to be calibrated. The lifetime of the clusters is stable and is not negatively affected by photobleaching thanks to the recording method of the invention which enables stable clusters to be formed in a glass medium.

When the fluorescence lifetime of the clusters is approximately a few nanoseconds, this enables the detectors of the microscopes to be calibrated with an equivalent precision with regard to the response times thereof.

A last example of a test chart 48 enables the system for positioning the sample holders of the microscope to be calibrated.

The various test charts described enable various types of calibration of microscopes but also of any other optical system such as optical detectors or optical sources.

The invention claimed is:

1. Method for 3D recording of data on a medium formed from a transparent photosensitive material including at least one dopant, said method including:
   a first step of calibrating and checking a first pulsed light source including calibrating the number of pulses, the level of fluence of each pulse emitted and the rate of the pulses; and
   a step of inscribing an area of the material,
   wherein the fluence of each pulse emitted, the number of pulses and the rate of the pulses are suitable for irradiating the material in said area such as to form fluorescent clusters stabilized from the dopant, each cluster forming a fluorescent emitter, the spectrum and the intensity of fluorescence of which correspond to a signature for encoding a data word, said stabilized clusters being obtained while minimizing the modification of the refractive index and the absorption coefficient of the medium in a wavelength range from visible to near infrared.

2. The data recording method according to claim 1, wherein the first source of light is calibrated such that:
   the rate of the pulses is greater than a second predetermined threshold for creating a temperature that is greater than a third temperature predetermined threshold in the irradiated area; and
   the duration of each emitted light pulse is shorter than the characteristic time of thermalization of the material such as to excite the area of the medium by multiphoton ionization.

3. The data recording method according to claim 1, wherein:
   the rate of each pulse of the first light source is greater than 1 kHz;
   the fluence of each pulse transmitted is substantially close to 1 J·cm$^{-2}$; and
   the wavelength of the laser is at least two times greater than the cut-off wavelength of the transparent medium.

4. The data recording method according to claim 1, wherein the first light source includes at least one of the two following light sources: an infrared femtosecond laser, and an infrared picosecond laser.

5. The data recording method according to claim 1, wherein the medium is formed from a glassy material and the dopant includes at least one type of metal ion of the set of following ions: silver ion, gold ion, and copper ion.

6. The data recording method according to claim 1, wherein the irradiation step comprises a set of pulses on a same area of the medium so as to form stable irradiated clusters, the formed clusters defining a fluorescent emitter, the spectrum and the intensity of fluorescence of which, corresponding to a given calibration of the first light source, defines a signature.

7. The data recording method according to claim 1, wherein the rate of the pulses of the first light source is substantially equal to 10 MHz.

8. The data recording method according to claim 1, wherein the steps of the recording method are repeated on a set of areas located at a same depth of the medium, the set of the areas located at a same depth being called a layer, each calibration of the first source being suitable for an inscription given on each of the areas, wherein the method can be repeated on superposed layers of the medium.

* * * * *